(12) United States Patent
Williams et al.

(10) Patent No.: US 6,887,900 B2
(45) Date of Patent: May 3, 2005

(54) NEMATICIDAL COMPOSITIONS AND METHODS

(75) Inventors: Deryck Jeremy Williams, St. Louis, MO (US); Andrew P. Kloek, St. Louis, MO (US); Michelle Coutu Hresko, Chesterfield, MO (US)

(73) Assignee: Divergence, Inc., St. Louis, MO (US)

( * ) Notice: Subject to any disclaimer, the term of this patent is extended or adjusted under 35 U.S.C. 154(b) by 0 days.

(21) Appl. No.: 10/090,527

(22) Filed: Mar. 4, 2002

(65) Prior Publication Data

US 2003/0166714 A1 Sep. 4, 2003

(51) Int. Cl.[7] .......................... A01N 37/06; A61K 31/22
(52) U.S. Cl. ..................................................... 514/549
(58) Field of Search .................................. 514/28, 549

(56) References Cited

U.S. PATENT DOCUMENTS

| | | | |
|---|---|---|---|
| 2,852,426 A | 9/1958 | Stansbury et al. ............ 167/22 |
| 3,608,085 A | 9/1971 | Papworth .................... 424/317 |
| 3,833,736 A | 9/1974 | Frick et al. ................. 424/343 |
| 3,895,116 A | 7/1975 | Herting et al. .............. 424/317 |
| 3,931,413 A | 1/1976 | Frick et al. ................. 424/318 |
| 3,983,214 A | 9/1976 | Misato et al. ............... 424/180 |
| 4,002,775 A | 1/1977 | Kabara ....................... 426/532 |
| 4,442,125 A | 4/1984 | Thiele ........................ 424/318 |
| 4,547,520 A | 10/1985 | Ide et al. .................... 514/450 |
| 4,663,364 A | 5/1987 | Iwasaki et al. ............. 523/122 |
| 4,826,678 A | 5/1989 | Gaudet et al. ................ 424/93 |
| 4,962,093 A | 10/1990 | Ohkawa et al. .............. 514/53 |
| 5,093,124 A | 3/1992 | Kulenkampff .............. 424/406 |
| 5,192,546 A | 3/1993 | Abercrombie .............. 424/405 |
| 5,246,716 A | 9/1993 | Sedun et al. ................ 424/713 |
| 5,277,708 A * | 1/1994 | Stuart, Jr. ....................... 106/8 |
| 5,342,630 A | 8/1994 | Jones ......................... 424/717 |
| 5,346,698 A | 9/1994 | Abercrombie .............. 424/405 |
| 5,395,851 A | 3/1995 | Sedun ........................ 514/494 |
| 5,432,146 A | 7/1995 | Winston ..................... 504/101 |
| 5,464,805 A | 11/1995 | Winston ..................... 504/101 |
| 5,496,568 A | 3/1996 | Winston ..................... 424/717 |
| 5,518,986 A | 5/1996 | Winston ..................... 504/101 |
| 5,518,987 A | 5/1996 | Winston ..................... 504/101 |
| 5,667,993 A | 9/1997 | Feitelson et al. ........... 435/91.2 |
| 5,668,292 A | 9/1997 | Somerville et al. |
| 5,670,365 A | 9/1997 | Feitelson ................. 435/252.3 |
| 5,674,897 A | 10/1997 | Kim et al. ................... 514/552 |
| 5,698,592 A | 12/1997 | Kim et al. ................... 514/552 |
| 5,707,938 A | 1/1998 | Rajamannan ............... 504/320 |
| 5,741,793 A | 4/1998 | Young et al. ................ 514/247 |
| 5,801,026 A | 9/1998 | Somerville et al. |
| 5,844,121 A | 12/1998 | Keller ........................ 800/205 |
| 5,942,661 A | 8/1999 | Keller ........................ 800/298 |
| 5,951,994 A | 9/1999 | Wada et al. ................ 424/405 |
| 5,965,793 A | 10/1999 | Broun et al. |
| 6,028,248 A | 2/2000 | Somerville et al. |
| 6,103,768 A | 8/2000 | Savage et al. .............. 514/627 |
| 6,124,275 A | 9/2000 | Emerson .................... 514/159 |
| 6,124,359 A | 9/2000 | Feitelson et al. ........... 514/552 |
| 6,136,856 A | 10/2000 | Savage et al. .............. 514/552 |
| 6,194,383 B1 | 2/2001 | Hammann et al. ............ 514/11 |
| 6,225,528 B1 | 5/2001 | Chin et al. |
| 6,291,742 B1 | 9/2001 | Somerville et al. |
| 6,310,194 B1 | 10/2001 | Somerville et al. |
| 6,329,518 B1 | 12/2001 | Green et al. |
| 6,333,488 B1 | 12/2001 | Lawrence et al. |

FOREIGN PATENT DOCUMENTS

| | | | |
|---|---|---|---|
| JP | 63215611 | * | 9/1988 |
| JP | 04112817 | * | 4/1992 |

OTHER PUBLICATIONS

Davis et al., "Nematicidal Activity of Fatty Acid Esters on Soybean Cyst and Root–knot Nematodes" J. of Nematology 29(4S):677–684, 1997.

Singh et al., "Transgenic Expression of A Delta–12–epoxygenase Gene in Arabidopsis Seeds Inhibits Accumulation of Linoleic Acid" Planta 212:872–879, 2001.

Singh et al., "Inhibition of Polyunsaturated Fatty Acid Accumulation in Plants Expressing a Fatty Acid Epoxygenase" Biochem. Soc. Trans. 28:940–942, 2000.

Stadler et al., "Fatty Acids and Other Compounds with Nematicidal Acitivty from Cultures of Basidiomycetes" Planta Med. 60:128–132, 1994.

Lee et al., "Identification of Non–Heme Diiron Proteins That Catalyze Triple Bond and Epoxy Group Formation" Science 280:915918, 1998.

* cited by examiner

*Primary Examiner*—Alton N. Pryor
(74) *Attorney, Agent, or Firm*—Fish & Richardson P.C.

(57) ABSTRACT

The invention concerns the use of certain compounds related to fatty acids to control nematodes that infest plants or the situs of plants. Nematodes parasitizing animals can also be controlled using the methods and composition of this invention. The useful compounds are inhibitors of nematode delta-12 fatty acid desaturases and can be, for example, from C16 to C20 in length. A feature of these compounds is that their inhibitory effect on the activity of a nematode delta-12 desaturase, or on the viability or fecundity of a nematode, is smaller in the presence of the product of a delta-12 fatty acid desaturase (e.g., linoleate) than in the presence of the substrate of the enzyme (e.g., oleate).

55 Claims, 5 Drawing Sheets

NEMATICIDAL COMPOSITIONS AND METHODS

BACKGROUND OF THE INVENTION

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts of plants, including roots, developing flower buds, leaves, and stems. Plant parasites are classified on the basis of their feeding habits into the broad categories, migratory ectoparasites, migratory endoparasites, and sedentary endoparasites. Sedentary endoparasites, which include the root knot nematodes (Meloidogyne) and cyst nematodes (Globodera and Heterodera) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) Plant and Soil Nematodes: Societal Impact and Focus for the Future. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control of soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) *Califonia Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22–24; U.S. Pat. No. 6,048, 714). The few available broad-spectrum nematicides such as Telone (1,3-dichloropropene+chloropicrin) have significant restrictions on their use because of toxicological concerns (Carter (2001)*California Agriculture* 55(3):12–18).

Fatty acids are a class of natural compounds that have been investigated as alternatives to the toxic, non-specific organophosphate, carbamate and fumigant pesticides (Stadler et al. (1994) *Planta Medica* 60(2):128–132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677–684). In view of this general mode of action it is not surprising that fatty acids are used in a variety of pesticidal applications including as herbicides (e.g., SCYTHE by Dow Agrosciences is the C9 saturated fatty acid pelargonic acid), as bacteriacides and fungicides (U.S. Pat. Nos. 4,771,571; 5,246,716) and as insecticides (e.g., SAFER INSECTICIDAL SOAP by Safer, Inc.).

The phytotoxicity of fatty acids has been a major constraint on their general use in agricultural applications (U.S. Pat. No. 5,093,124) and the mitigation of these undesirable effects while preserving pesticidal activity is a major area of research. The esterification of fatty acids can significantly decrease their phytotoxicity (U.S. Pat. Nos. 5,674,897; 5,698,592; 6,124,359). Such modifications can however lead to dramatic loss of nematicidal activity as is seen for linoleic, linolenic and oleic acid (Stadler et al. (1994) *Planta Medica* 60(2):128–132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S):677–684). This is the expected result if both the phytotoxicity and the nematicidial activity derive from the non-specific disruption of plasma membrane integrity. Similarly the rapid onset of pesticidal activity seen with many nematicidal fatty acids at therapeutic concentrations (U.S. Pat. Nos. 5,674,897; 5,698,592; 6,124,359) suggests a non-specific mechanism of action, possibly related to the disruption of membranes, action potentials and neuronal activity.

Ricinoleic acid, the major component of castor oil, provides another example of the unexpected effects esterification can have on fatty acid activity. Ricinoleic acid has been shown to have an inhibitory effect on water and electrolyte absorption using everted hamster jejunal and ileal segments (Gaginella et al. (1975) *J Pharmacol Exp Ther* 195(2):355–61) and to be cytotoxic to isolated intestinal epithelial cells (Gaginella et al. (1977) J Pharmacol Exp Ther 201(1):259–66). These features are likely the source of the laxative properties of castor oil which is given as a purgative in humans and livestock (e.g., castor oil is a component of some de-worming protocols because of its laxative properties). In contrast, the methyl ester of ricinoleic acid is ineffective at suppressing water absorption in the hamster model (Gaginella et al. (1975) *J Pharmacol Exp Ther* 195(2):355–61).

The macrocyclic lactones (e.g., avermectins and milbemycins) and delta-toxins from *Bacillus thuringiensis* (Bt) are chemicals that in principle provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1–2):217–225;

Wright & Perry (1998) *Musculature and Neurobiology*. In: The Physiology and Biochemistry of Free-Living and Plant-parasitic Nematodes (eds. Perry & Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt toxins must be ingested to affect their target organ the brush border of midgut epithelial cells (Marroquin et al. (2000) *Genetics*. 155(4):1693–1699). Consequently they are not anticipated to be effective against the dispersal, non-feeding, juvenile stages of plant parasitic nematodes in the field. These juvenile stages only commence feeding when a susceptible host has been infected, thus effective nematicides must be able to penetrate the cuticle. In addition, soil mobility of a relatively large 65–130 kDa protein—the size of typical Bt delta toxins—is expected to be poor and delivery in planta is likely to be constrained by the exclusion of large particles by the feeding tube of certain plant parasitic nematodes such as Heterodera (Atkinson et al. (1998) Engineering resistance to plant-parasitic nematodes. In: The Physiology and Biochemistry of Free-Living and Plant-parasitic Nematodes (eds Perry & Wright), CAB International 1998).

Many plant species are known to be highly resistant to nematodes. The most well documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family *Asteraceae* (family *Compositae*) (Hackney & Dickerson. (1975) *J Nematol* 7(1):84–90). The active principle(s) for this nematicidal activity has not been discovered in all of these examples and no plant-derived products are sold commercially for control of nematodes. In the case of the *Asteraceae*, the photodynamic compound alpha-terthienyl has been shown to account for the strong nematicidal activity of the roots. In the case of castor beans they are plowed under as a green manure before a seed crop is set. A significant drawback of the castor plant is that the seed contains toxic compounds (such as ricin) that can kill humans, pets, and livestock and is also highly allergenic.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Two factors contribute to the need for novel anthelmintics and vaccines for control of parasitic nematodes of animals. First, some of the more prevalent species of parasitic nematodes of livestock are building resistance to the currently available anthelmintic drugs, meaning that these products will eventually lose their efficacy. These developments are not surprising because few effective anthelmintic drugs are available and most have been used continuously. Presently a number of parasitic species has developed resistance to most of the anthelmintics (Geents et al. (1997) *Parasitology Today* 13:149–151; Prichard (1994) *Veterinary Parasitology* 54:259–268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141–146). Secondly, there are some issues with toxicity for the major compounds currently available.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include hookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides*, the large gut roundworm infects more than one billion people worldwide and causes malnutrition and obstructive bowl disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

While public health measures have nearly eliminated one tropical nematode (the water-borne Guinea worm), cases of other worm infections have actually increased in recent decades. In these cases, drug intervention provided through foreign donation or purchased by those who can afford it remains the major means of control. Because of the high rates of reinfection after drug therapy, vaccines remain the best hope for worm control in humans. There are currently no vaccines available.

Until safe and effective vaccines are discovered to prevent parasitic nematode infections, anthelmintic drugs will continue to be used to control and treat nematode parasitic infections in both humans and domestic animals. Finding effective compounds against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.* 28(3): 395–411). The genome of *C. elegans* has been completely sequenced and the nematode shares many general developmental and basic cellular processes with vertebrates (Ruvkin et al. (1998) *Science* 282: 2033–41). This, together with its short generation time and ease of culturing, has made it a model system of choice for higher eukaryotes (Aboobaker et al. (2000) *Ann. Med.* 32: 23–30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028–33). The latter property is of particular relevance given that the avermectin class of drugs is thought to act at glutamate-gated chloride receptors and is highly selective for invertebrates (Martin (1997) *Vet. J.* 154:11–34).

A subset of the genes involved in nematode specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J Mol. Biol.* 246:500–10; Redmond et al. (2001) *Mol. Biochem. Parasitol.* 112:125–131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806–811; Montgomery et al. (1998) *Proc. Natl. Acad Sci USA* 95(26):15502–15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

The present invention describes compositions which show surprising nematicidal activity in part due to selective inhibition of metabolic processes demonstrated to be essential to nematodes and either absent or non-essential in vertebrates and plants. This invention therefore provides urgently needed compounds and methods for the environmentally safe control of parasitic nematodes.

SUMMARY

The invention concerns compositions and processes for controlling nematodes. In one embodiment, the subject invention comprises the use of certain compounds related to fatty acids to control nematodes that infest plants or the situs of plants. Nematodes parasitizing animals can also be controlled using the methods and composition of this invention. The useful compounds are inhibitors of nematode delta-12 fatty acid desaturases (also referred to herein as a nematode delta-12 desaturases) and can be from C16 to C20 in length. A feature of these compounds is that their inhibitory effect on the activity of a nematode delta-12 desaturase, or on the viability or fecundity of a nematode, is smaller in the presence of the product of a delta-12 fatty acid desaturase (e.g., linoleate) than in the presence of the substrate of the enzyme (e.g., oleate). For these competition experiments the substrate (e.g., oleate) and the product (e.g., linoleate) are used in equivalent amounts. These effects can be demonstrated on a delta-12 fatty acid desaturase (also referred to herein as a delta-12 desaturase) protein in vitro, on transgenic cells containing delta-12 desaturases or on intact organisms (e.g., a nematode) containing delta-12 desaturases. In one embodiment of this test, the inhibitor, substrate and product of the delta-12 desaturase are present in equal concentrations. The useful fatty acid-related compounds can be, for example, a epoxide, cyclopropane, cyclopropene, methylated, or hydroxylated form. The compounds can also contain sulfur in place of carbon at certain positions. In a preferred embodiment of the subject invention, delta-12 desaturase inhibiting fatty acid esters are used.

Preferred fatty acid esters useful according to the subject invention are C16 to C20 in length, have a cis (Z) carbon double bond at the delta-9 position (i.e., between C9 and C10 counting from the carbonyl carbon (C=O)) and a variety of modifications at the C12, C13 or both C12 and C13 positions. Preferred fatty acid esters also include thia fatty acid esters with sulfur in place of carbon at positions 12, 13 or 12 and 13. Most preferred compounds are C16 to C18 in length. Examples include, ricinoleic acid methyl ester (12-hydroxy-cis-9-octadecenoic acid methyl ester), vernolic acid methyl ester ((12,13)-epoxy-cis-9-octadecenoic acid methyl ester) and crepenynic acid methyl ester (9(Z)-octadecen-12-ynoic acid methyl ester). Specifically excluded are the normal substrates of delta-12 desaturases (e.g., cis-9-octadecenoate (oleate), cis-9-hexadecenoate (palmitoleate) and the normal products of delta-12 desaturases (e.g., cis-9,12-octadecadienoate (linoleate), cis-9,12-hexadecadienoate). Fatty acid compounds where the only modifications are a single cis double bond at the delta-9 position (cis double bond between C9 and C10), or single double bonds at the delta-9 (cis double bond between C9 and C10) and delta-12 positions (cis double bond between C12 and C13) as well as certain naturally occurring esters such as triglycerides, diacylglycerides and phospholipids are generally not preferred. Examples of preferred sulfur containing fatty acid analogs include methyl 12-thia-oleate and methyl 13-thia-oleate.

The invention also features compounds that are relatively selective inhibitors of one or more nematode delta-12 desaturase polypeptides relative to one or more plant or animal fatty acid desaturase-like polypeptides. The compounds can have a Ki for a nematode fatty acid desaturase that is 10-fold, 100-fold, 1,000-fold or more lower than for a plant or animal fatty acid desaturase-like polypeptides, e.g., a host plant or host animal of the nematode. The invention further features relatively non-selective inhibitors as well as completely non-selective inhibitors.

In yet another aspect, the invention features a method of treating a disorder (e.g., an infection) caused by a nematode, (e.g., *M. incognita, H. glycines, H. contortus, A. suum*) in a subject, e.g., a host plant or host animal. The method includes administering to the subject an effective amount of an inhibitor of a delta-12 desaturase polypeptide activity or an inhibitor of expression of a delta-12 desaturase polypeptide or an inhibitor that impairs the modification of a delta-12 desaturase resulting in change in the activity or localization of the desaturase. The inhibitor may be delivered by several means including as a feed additive, as a pill or by injection.

In still another aspect, methods of inhibiting a nematode (e.g., *M. incognita, H. glycines, H. contortus, A. suum*) delta-12 desaturase(s) are provided. Such methods can include the steps of: (a) providing a nematode that contains a delta-12 fatty acid desaturase-like gene; (b) contacting the nematode with fatty acid analogs or other compounds that inhibit the enzyme. Also provided are methods of rescuing the effect of the inhibitor. Such methods comprise the steps of: (a) inhibiting the enzyme and (b) providing delta-12 unsaturated fatty acids exogenously (e.g, linoleate).

In another aspect, methods of reducing the viability or fecundity or slowing the growth or development or inhibiting the infectivity of a nematode using a fatty acid analog or inhibitor of a delta-12 desaturase are provided. Such methods comprise the steps of (a) providing a nematode that contains a delta-12 desaturase-like gene; (b) contacting the nematode with specific inhibitory fatty acid analogs or inhibitors of a delta-12 fatty acid desaturase; (c) reducing the viability or fecundity of the nematode. Also provided are methods of rescuing the effect of the fatty acid desaturase inhibitors or other inhibitors. Such methods can involve contacting the nematode with delta-12 unsaturated fatty acids exogenously.

The invention features a method for reducing the viability, growth, or fecundity of a nematode, the method comprising exposing the nematode to an agent that inhibits the activity of a fatty acid desaturase-like polypeptide (e.g., a delta-12 fatty acid desaturase) and a method for protecting a plant from a nematode infection, the method comprising applying to the plant, to the soil, or to seeds of the plant an inhibitor of a nematode fatty acid desaturase-like polypeptide. The invention also features a method for protecting a mammal from a nematode infection, the method comprising administering to the mammal an inhibitor of a nematode fatty acid desaturase-like polypeptide (e.g., a delta-12 fatty acid desaturase). In preferred embodiments the inhibitor does not significantly inhibit the activity of a fatty acid desaturase-like polypeptide expressed by the plant or at least does not do so to the extent that the growth of the plant is significantly impaired.

The invention process is particularly valuable to control nematodes attacking the roots of desired crop plants, ornamental plants, and turf grasses. The desired crop plants can be, for example, soybeans, cotton, strawberries, tomatoes, banana, sugar cane, sugar beet, potatoes, or citrus.

Thus, the invention features a composition, e.g., a nematicidal composition, comprising: (a) an effective amount of a compound having the formula:

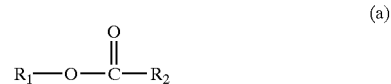

(a)

wherein: $R_1$=a $C_1$–$C_5$ singly or multiply substituted or unsubstituted carbon chain, wherein the substituants are selected from the group consisting of: hydroxy, halogen, amino, cyano, a singly or multiply substituted or unsubstituted $C_1$–$C_2$ carbon chain, cyclopropane, and epoxy; and $R_2$=a $C_{15}$–$C_{19}$ singly or multiply substituted or unsubstituted carbon chain having a cis double bond between the $9^{th}$ and $10^{th}$ carbons counting form the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituants are selected from the group consisting of hydroxy, halogen, amino, cyano, a singly or multiply substituted or unsubstituted $C_1$–$C_2$ carbon chain, cyclopropane, cyclopropene, and epoxy; and (b) an aqueous surfactant.

In certain embodiments, $R_1$=a $C_1$–$C_5$ singly or multiply substituted or unsubstituted carbon chain, wherein the substituants are selected from the group consisting of: hydroxy, halogen, amino, cyano, an unsubstituted $C_1$–$C_2$ carbon chain, cyclopropane, and epoxy. In other embodiments, $R_2$=a $C_{15}$–$C_{19}$ singly or multiply substituted or unsubstituted carbon chain having a cis double bond between the $9^{th}$ and $10^{th}$ carbons counting form the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituants are selected from the group consisting of hydroxy, halogen, amino, cyano, a unsubstituted $C_1$–$C_2$ carbon chain, cyclopropane, cyclopropene, and epoxy; the C1–C2 carbon chain of one or both of $R_1$ and $R_2$ is singly or multiple substituted and the substituants are selected from the group consisting of: hydroxy, halogen, amino, cyano, and epoxy. In certain embodiments: the $C_1$–$C_2$ carbon chain of one or both of $R_1$ and $R_2$ is singly or multiple substituted and the substituants are selected from the group consisting of: hydroxy, halogen, and amino; the $C_1$–$C_2$ carbon chain of $R_1$ is singly substituted; the $C_1$–$C_2$ carbon chain of $R_2$ is singly substituted; and $R_1$ =a singly or multiply substituted C1 carbon chain $R_1$ is a $C_1$–$C_2$ substituted or unsubstituted carbon chain.

In other embodiments, $R_2$ is substituted only at one or both of $12^{th}$ and $13^{th}$ carbons counting from the carbonyl carbon; $R_2$ is substituted only at the $12^{th}$ carbon counting from the carbonyl carbon; $R_2$ is substituted only at the $13^{th}$ carbon counting from the carbonyl carbon; wherein within $R_2$ there is a triple bond between the $12^{th}$ and $13^{th}$ carbons counting from the carbonyl carbon; and within $R_2$ the substituants are selected from the group consisting of: hydroxy, epoxy, and a $C_1$ methyl.

The invention also features a nematicidal composition comprising: (a) a fatty acid methyl ester selected from the group consisting of: ricinoleic acid methyl ester, crepenynic acid methyl ester, and vernolic acid methyl ester; and (b) an aqueous surfactant. In certain embodiments, the aqueous surfactant is selected from the group consisting of: ethyl lactate, Tween 20 and Igepal CO 630; the composition comprises a permeation enhancer, e.g., a cyclodextrin. A permeation enhancer is generally an agent that permits the active compounds the invention, e.g., the fatty acid esters of the invention, to pass through cellular membranes.

The composition can further include a co-solvent, e.g., isopropanol. A co-solvent (i.e., a latent solvent or indirect solvent) is an agent that becomes an effective solvent in the presence of an active solvent.

The compositions can also include one more nematicides such as an avermectin, ivermectin, and milbemycin.

The invention features methods for controlling nematodes by administering a delta-12 fatty acid desaturase. Thus, the invention includes a method for control of unwanted nematodes, the method comprising administering to mammals, plants, seeds or soil a nematicidal composition comprising: (a) an effective amount of a compound having the formula

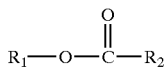

wherein: $R_1$=a $C_1$–$C_5$ singly or multiply substituted or unsubstituted carbon chain, wherein the substituents are selected from the group consisting of: hydroxy, halogen, amino, cyano, a singly or multiply substituted or unsubstituted $C_1$–$C_2$ carbon chain, cyclopropane, and epoxy; and $R_2$=a $C_{15}$–$C_{19}$ singly or multiply substituted or unsubstituted carbon chain having a cis double bond between the $9^{th}$ and $10^{th}$ carbons counting form the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituents are selected from the group consisting of hydroxy, halogen, amino, cyano, a singly or multiply substituted or unsubstituted $C_1$–$C_2$ carbon chain, cyclopropane, cyclopropene, and epoxy; and (b) an aqueous surfactant.

In certain methods of the invention: $R_1$=a $C_1$–$C_5$ singly or multiply substituted or unsubstituted carbon chain, wherein the substituents are selected from the group consisting of: hydroxy, halogen, amino, cyano, a unsubstituted $C_1$–$C_2$ carbon chain, cyclopropane, and epoxy; $R_2$=a $C_{15}$–$C_{19}$ singly or multiply substituted or unsubstituted carbon chain having a cis double bond between the $9^{th}$ and $10^{th}$ carbons counting form the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituents are selected from the group consisting of hydroxy, halogen, amino, cyano, a unsubstituted $C_1$–$C_2$ carbon chain, cyclopropane, cyclopropene, and epoxy; the $C_1$–$C_2$ carbon chain of one or both of $R_1$ and $R_2$ is singly or multiple substituted and the substituents are selected from the group consisting of: hydroxy, halogen, amino, cyano, and epoxy; the $C_1$–$C_2$ carbon chain of one or both of $R_1$ and $R_2$ is singly or multiple substituted and the substituents are selected from the group consisting of: hydroxy, halogen, and amino; the $C_1$–$C_2$ carbon chain of $R_1$ is singly substituted; the $C_1$–$C_2$ carbon chain of $R_2$ is singly substituted; $R_1$ is a $C_1$–$C_2$ substituted or unsubstituted carbon chain; $R_2$ is substituted only at one or both of $12^{th}$ and $13^{th}$ carbons counting from the carbonyl carbon; $R_2$ is substituted only at the $12^{th}$ carbon counting from the carbonyl carbon; $R_2$ is substituted only at the $13^{th}$ carbon counting from the carbonyl carbon; wherein within $R_2$ there is a triple bond between the $12^{th}$ and $13^{th}$ carbons counting from the carbonyl carbon; and within $R_2$ the substituants are selected from the group consisting of: hydroxy, epoxy, and a $C_1$ methyl.

The invention also features a method for control of unwanted nematodes comprising administering to mammals, plants, seeds or soil a nematicidal composition comprising an effective amount of: (a) a fatty acid methyl ester selected from the group consisting of: ricinoleic acid methyl ester, crepenynic acid methyl ester, and vernolic acid methyl ester; and (b) an aqueous surfactant.

In certain embodiments of the method the aqueous surfactant is selected from the group consisting of: ethyl lactate, Tween 20 and Igepal CO 630; 37; the composition comprises a permeation enhancer (e.g., a cyclodextrin); the composition comprises a co-solvent (e.g., isopropanol); the method includes administering a nematicide selected from the group consisting of: avermectins, ivermectin, and milbemycin; the nematode infects plants and the nematicidal composition is applied to the soil or to plants; the nematicidal composition is applied to soil before planting; the nematicidal composition is applied to soil after planting; the nematicidal composition is applied to soil using a drip system; the nematicidal composition is applied to soil using a drench system; the nematicidal composition is applied to plant roots; the nematicidal composition is applied to seeds; the nematode infects a mammal; the nematicidal composition is administered to non-human mammal; the nematicidal composition is administered to a human; the nematicidal composition is formulated as a drench to be administered to a non-human animal; the nematicidal composition is formulated as an orally administered drug; and the nematicidal composition is formulated as an injectable drug.

The invention also features feeds that have been supplemented to include one or more delta 12 fatty acid desaturase inhibitors. The feeds may also be treated to reduce the amount of delta 12 fatty acid desaturase substrates or products in the feed. More generally, the feed can be treated to reduce the content of fatty acids that act to complement the loss of a delta 12 fatty acid desaturase.

Thus, the invention features a nematicidal feed for a non-human mammal comprising: (a) an animal feed; (b) an effective amount of a nematicidal compound having the formula

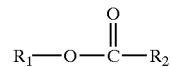

wherein: $R_1$=a $C_1$–$C_5$ substituted or unsubstituted carbon chain, wherein the substituents are selected from the group consisting of: hydroxy, halogen, amino, cyano, a singly or multiply substituted or unsubstituted $C_1$–$C_2$ carbon chain, cyclopropane, and epoxy; and $R_2$=a $C_{15}$–$C_{19}$ substituted or unsubstituted carbon chain having a cis double bond between the $9^{th}$ and $10^{th}$ carbons and either: (i) a triple bond between the $12^{th}$ and $13^{th}$ carbons or (ii) either a single or double bond between the $12^{th}$ and $13^{th}$ carbons and at least one substituant at one or both of the $12^{th}$ and $13^{th}$ carbons, wherein the substituents are selected from the group consisting of: hydroxy, halogen, amino, cyano, a singly or multiply or unsubstituted $C_1$–$C_2$ carbon chain, cyclopropane, cyclopropene, and epoxy; and (c) an aqueous surfactant.

The feed can be treated to reduce linoleic acid content, linolenic acid content or both and the feed can be treated to reduced one or both of the gamma linolenic acid content and the alpha linolenic acid content have been reduced. The feed can be selected from the group consisting of: soy, wheat, corn, sorghum, millet, alfalfa, clover, and rye.

The invention also features a nematicidal composition comprising: (a) an effective amount of a compound having the formula

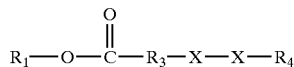

wherein: $R_1$=a $C_1$–$C_5$ substituted or unsubstituted carbon chain, wherein the substituents are selected from the group consisting of: hydroxy, halogen, amino, cyano, a singly or multiply substituted or unsubstituted $C_1$–$C_2$ carbon chain, cyclopropane, and epoxy; $R_3$=a $C_{11}$ substituted or unsubstituted carbon chain having a cis double bond between the $9^{th}$ and $10^{th}$ carbons counting form the carbonyl carbon, wherein the substituants are selected from the group consisting of hydroxy, halogen, amino, cyano, a singly or multiply or unsubstituted $C_1$–$C_2$ carbon chain, cyclopropane, cyclopropene, and epoxy; $R_4$=a $C_2$–$C_6$ substituted or unsubstituted carbon chain wherein the substituants are selected from the group consisting of: hydroxy, halogen, amino, cyano, a singly or multiply substituted or unsubstituted $C_1$–$C_2$ carbon chain, cyclopropane, and epoxy; X and Y are independently a substituted or unsubstituted methyl or S, provided at least one or X and Y is S and wherein the substituants on the methyl selected from the group consisting of: halogen, hydrogen, amino, and hydroxy; and (b) an aqueous surfactant. In certain embodiments, one of X and Y is $CH_2$.

The invention also features a nematicidal composition comprising (a) an effective amount of a compound having the formula

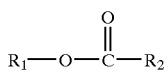

wherein: $R_1$=a $C_1$–$C_5$ substituted or unsubstituted carbon chain, wherein the substituents are selected from the group consisting of: hydroxy, halogen, amino, cyano, a singly or multiply substituted or unsubstituted $C_1$–$C_2$ carbon chain, cyclopropane, and epoxy; and $R_2$=a $C_{15}$–$C_{19}$ substituted or unsubstituted carbon chain having a single bond between the $9^{th}$ and $10^{th}$ carbons counting form the carbonyl carbon and either: (i) a triple bond between the $12^{th}$ and $13^{th}$ carbons or (ii) either a single or double bond between the $12^{th}$ and $13^{th}$ carbons and at least one substituant at one or both of the $12^{th}$ and $13^{th}$ carbons, wherein the substituents are selected from the group consisting of hydroxy, halogen, amino, cyano, a substituted or unsubstituted $C_1$–$C_2$ carbon chain, cyclopropane, cyclopropene, and epoxy; and (b) an aqueous surfactant.

In certain embodiments $R_2$=a $C_{15}$–$C_{19}$ substituted or unsubstituted carbon chain having a single bond between the $9^{th}$ and $10^{th}$ carbons and a single bond between the $12^{th}$ and $13^{th}$ carbons and at least one substituant at one or both of the $12^{th}$ and $13^{th}$ carbons, wherein the substituents are selected from the group consisting of hydroxy, halogen, amino, cyano, a singly or multiply or unsubstituted $C_1$–$C_2$ carbon chain, cyclopropane, cyclopropene, and epoxy; the $12^{th}$ and $13^{th}$ carbons are substituted with an epoxy group; and the $12^{th}$ carbon is substituted with a hydroxy group.

A "purified polypeptide", as used herein, refers to a polypeptide that has been separated from other proteins, lipids, and nucleic acids with which it is naturally associated. The polypeptide can constitute at least 10, 20, 50, 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the BLASTN and BLASTX programs (version 2.0 and 2.1) of Altschul et al. (1990). *J. Mol Biol.* 215:403–10. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al. (1997) *Nucleic Acids Res.* 25:3389–3402. When utilizing BLAST and Gapped BLAST programs for the determination of percent identity of amino acid sequences or nucleotide sequences, the default parameters of the respective programs can be used. The programs are available on the world wide web at: ncbi.nlm.nih.gov.

As used herein, the term "transgene" means a nucleic acid sequence (encoding, e.g., one or more subject polypeptides), which is partly or entirely heterologous, i.e., foreign, to the transgenic plant, animal, or cell into which it is introduced, or, is homologous to an endogenous gene of the transgenic plant, animal, or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as a leaf, root, seed, or stem.

As used herein, the terms "hybridizes under stringent conditions" and "hybridizes under high stringency conditions" refers to conditions for hybridization in 6×sodium chloride/sodium citrate (SSC) buffer at about 45° C., followed by two washes in 0.2×SSC buffer, 0.1% SDS at 60*C or 65*C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "anthelmintic activity" is an agent, which when tested, has measurable nematode-killing activity or results in reduced fertility or sterility in the nematodes such that fewer viable or no offspring result, or compromises the ability of the nematode to infect or reproduce in its host, or interferes with the growth or development of a nematode. The agent may also display nematode repellant properties. In the assay, the agent is combined with nematodes, e.g., in a well of microtiter dish, in liquid or solid media or in the soil containing the agent. Staged adult nematodes are placed on the media. The time of survival, viability of offspring, and/or the movement of the nematodes are measured. An agent with "anthelminthic activity" can, for example, reduce the survival time of adult nematodes relative to unexposed similarly staged adults, e.g., by about 20%, 40%, 60%, 80%, or more. In the alternative, an agent with "anthelminthic activity" may also cause the nematodes to cease replicating, regenerating, and/or producing viable progeny, e.g., by about 20%, 40%, 60%, 80%, or more. The effect may be apparent immediately or in successive generations.

As used herein, the term "binding" refers to the ability of a first compound and a second compound that are not covalently linked to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly a fatty acid desaturase-like or fatty acid desaturase activity (e.g., the ability to introduce a double bond at the delta-12 position of a fatty acid). The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is, for example, less than 0.05.

Unless otherwise specified, a "substituted" carbon, carbon chain, or methyl, alkyl can have one or more hydrogens replaced by another group, e.g., a halogen or a hydroxyl group.

In part, the delta-12 desaturase fatty acid analog inhibitors described herein provide an effective, environmentally safe means of inhibiting nematode metabolism, growth, viability, fecundity, development, infectivity and/or the nematode life-cycle. The compounds may be used alone or in combination with other nematicidal agents. The reduced phytotoxicity at active concentrations (i.e., greater therapeutic window) compared to prior art nematicidal fatty acid compounds allows for application post-planting and reduced handling costs providing economic incentives in addition to the environmental benefits.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
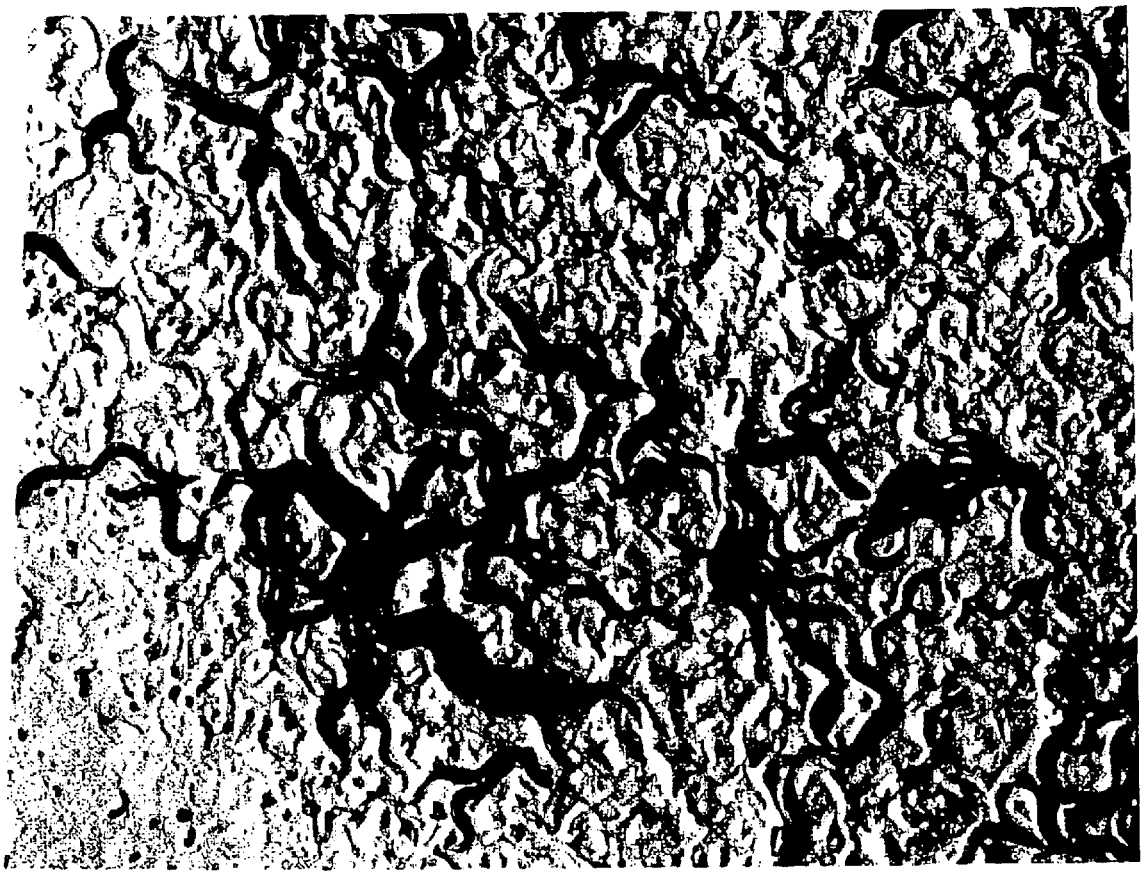
FIG. 1 is a photograph of *C. elegans* grown on oleic acid methyl ester.
Figure 2:
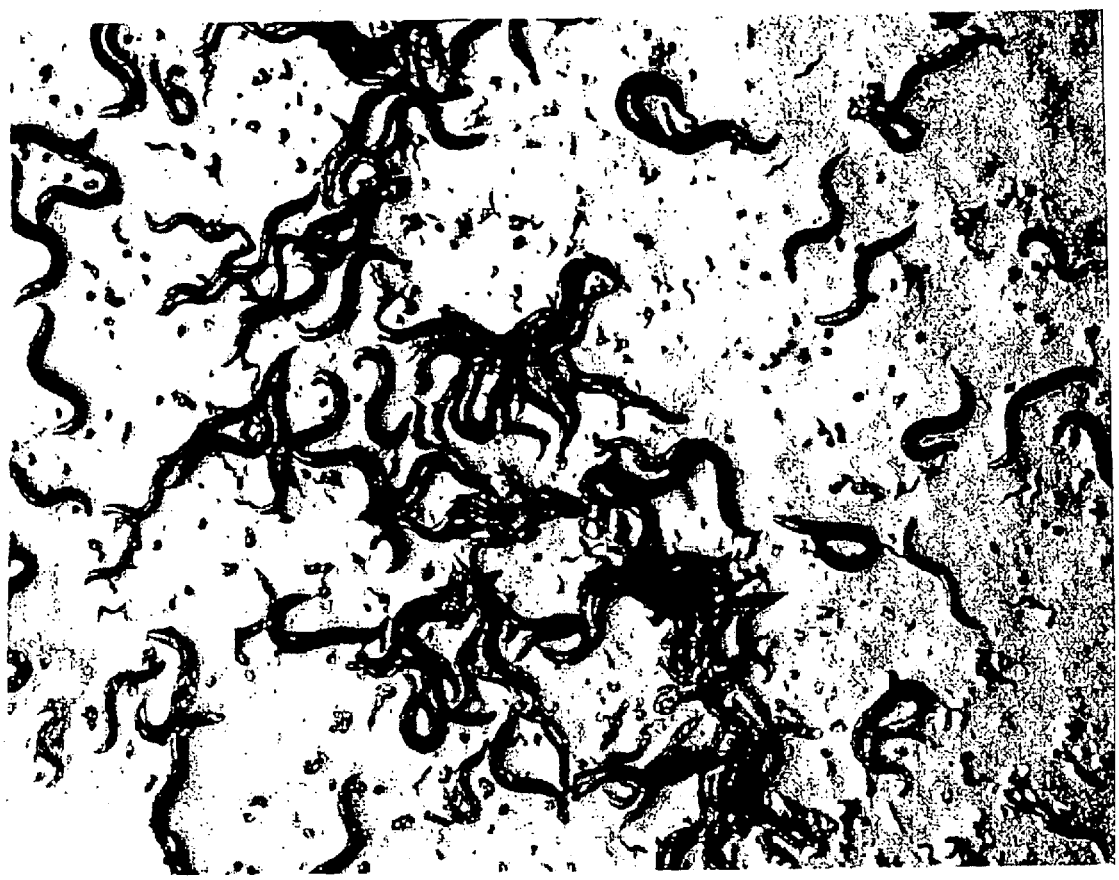
FIG. 2 is a photograph of *C. elegans* grown on linoleic acid methyl ester.
Figure 3:
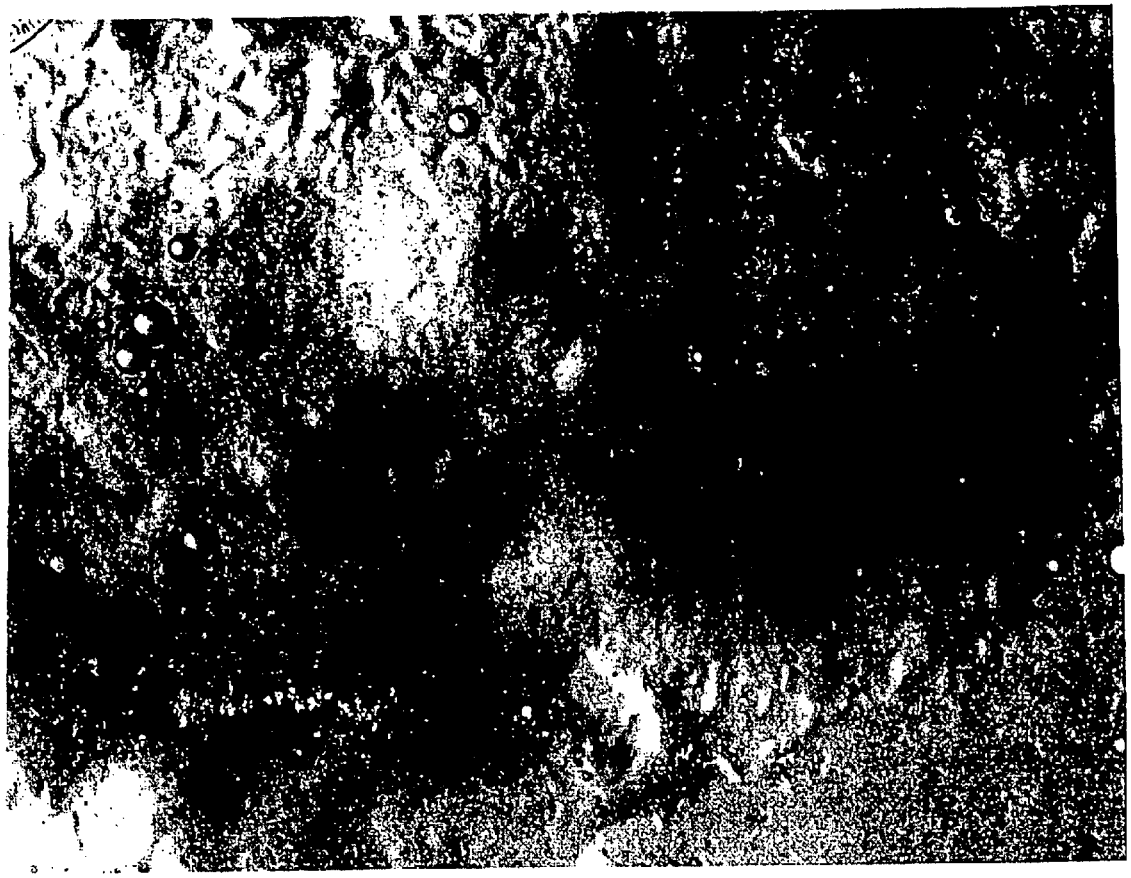
FIG. 3 is a photograph of *C. elegans* grown on ricinoleic acid methyl ester.
Figure 4:
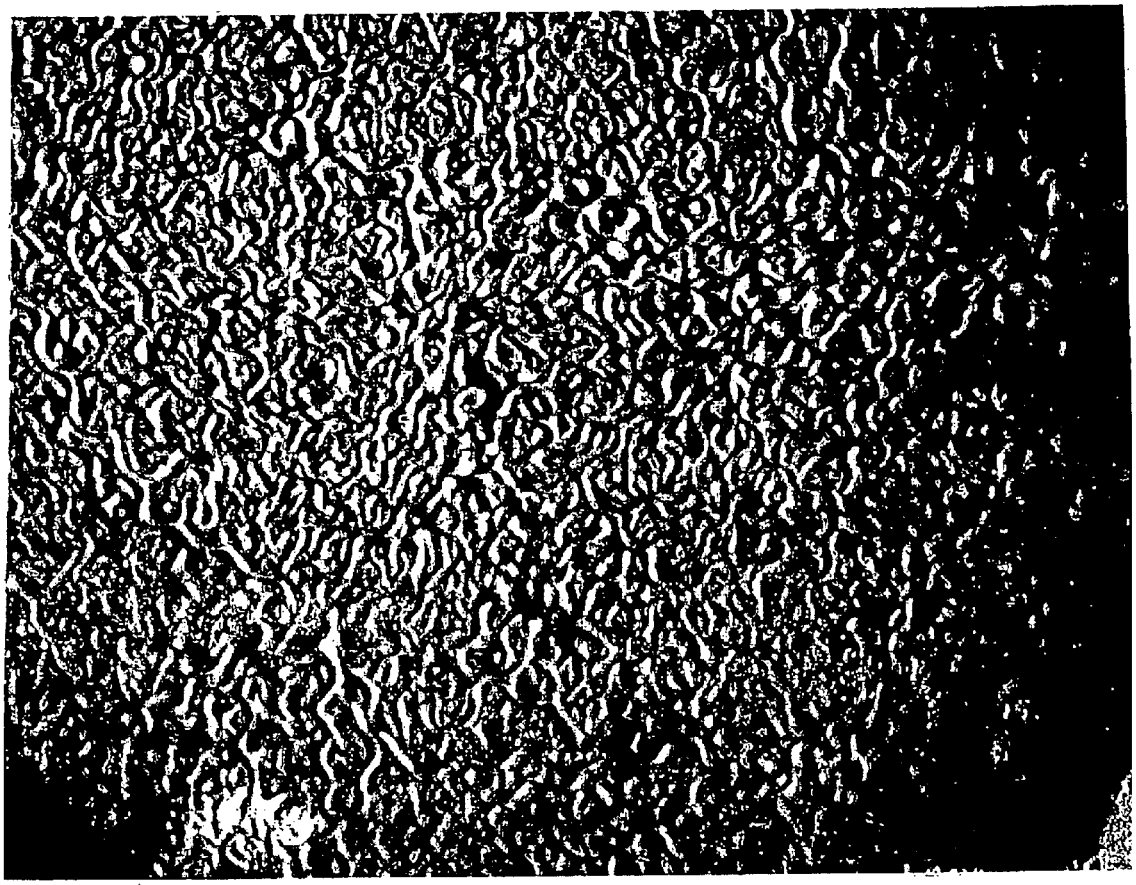
FIG. 4 is a photograph of *C. elegans* grown on vernolic acid methyl ester.

Described below are experiments demonstrating that delta-12 fatty acid desaturase activity is essential for nematode viability. Also described below are fatty acid analog inhibitors of delta-12 fatty acid desaturase.

Unsaturated fatty acids are essential to the proper functioning of biological membranes. At physiological temperatures, polar glycerolipids that contain only saturated fatty acids cannot form the liquid-crystalline bilayer that is the fundamental structure of biological membranes. The introduction of an appropriate number of double bonds (a process referred to as desaturation) into the fatty acids of membrane glycerolipids decreases the temperature of the transition from the gel to the liquid-crystalline phase and provides membranes with necessary fluidity. Fluidity of the membrane is important for maintaining the barrier properties of the lipid bilayer and for the activation and function of certain membrane bound enzymes. There is also evidence that unsaturation confers some protection to ethanol and oxidative stress, suggesting that the degree of unsaturation of membrane fatty acids has importance beyond temperature adaptation. Unsaturated fatty acids are also precursors of polyunsaturated acids (PUFAs) arachidonic and eicosapentaenoic acids in animals, which are important sources of prostaglandins. These molecules are local hormones that alter the activities of the cells in which they are synthesized and in adjoining cells, mediating processes in reproduction, immunity, neurophysiology, thermobiology, and ion and fluid transport.

The ability of cells to modulate the degree of unsaturation in their membranes is primarily determined by the action of fatty acid desaturases. Desaturase enzymes introduce unsaturated bonds at specific positions in their fatty acyl chain substrates, using molecular oxygen and reducing equivalents from NADH (or NADPH) to catalyze the insertion of double bonds. In many systems, the reaction uses a short electron transport chain consisting of NAD(P)H, cytochrome b5 reductase, and cytochrome b5, to shuttle electrons from NAD(P)H and the carbon-carbon single bond to oxygen, forming water and a double bond (C=C). Many eukaryotic desaturases are endoplasmic reticulum (ER) bound nonheme diiron-oxo proteins which contain three conserved histidine-rich motifs and two long stretches of hydrophobic residues. These hydrophobic alpha helical domains are thought to position the protein with its bulk exposed to the cytosolic face of the ER and to organize the active site histidines to appropriately coordinate the active diiron-oxo moiety.

While most eukaryotic organisms, including mammals, can introduce a double bond into an 18-carbon fatty acid at the D9 position, mammals are incapable of inserting double bonds at the DELTA-12 or D15 positions. For this reason, linoleate (18:2 D9,12) and linolenate (18:3 D9,12,15) must be obtained from the diet and, thus, are termed essential fatty acids. These dietary fatty acids come predominately from plant sources, since flowering plants readily desaturate the DELTA-12 and the D15 positions. Certain animals, including some insects and nematodes, can synthesize de novo all their component fatty acids including linoleate and linolenate. The nematode *C. elegans*, for example, can synthesize de novo a broad range of polyunsaturated fatty acids including arachidonic acid and eicosapentaenoic acids, a feature not shared by either mammals or flowering plants (Spychalla et al. (1997) Proc. Natl. Acad. Sci USA 94(4):1142–7).

The *C. elegans* desaturase gene fat-2 has been expressed in *S. cerevisiae* and shown to be delta-12 fatty acid desaturase (Peyou-Ndi et al. (2000) Arch. Biochem. Biophys. 376(2):399–408). This enzyme introduces a double bond between the 12th and the 13th carbons (from the carboxylate end) and can convert the mono-unsaturated oleate (18:1 D9) and palmitoleate (16:1 D9) to the di-unsaturated linoleate (18:2 D9,12) and 16:2 D9,12 fatty acids, respectively.

The nematode delta-12 enzymes are potentially good targets for anti-nematode compounds for several reasons. Firstly, as mentioned above, mammals are thought not to have delta-12 fatty acid desaturases. In addition, the enzymes appear to be phylogenetically diverged from their homologs in plants, having less than 40% pairwise sequence identity at the amino acid level and phylogenetic analyses demonstrate clustering of nematode delta-12 and w-3 desaturases away from homologs in plants. Experiments with both transgenic *Arabidopsis* and soybeans reveal that plants can tolerate significant reductions in linoleate or linolenate, suggesting that inhibitors of delta-12 desaturases would likely not be toxic to plants (Miquel & Browse (1992) *J. Biol. Chem.* 267(3):1502–9; Singh et al. (2000) *Biochem. Society Trans.* 28: 940–942; Lee et al. (1998) *Science* 280:915–918). Thus, inhibitors of the enzyme are likely to be non-toxic to mammals. Importantly, as detailed herein, a delta-12 fatty acid desaturase of nematodes has been shown to be essential to their viability, both through inhibitor and RNA-mediated interference studies. Thus, delta-12 fatty acid desaturases could serve as ideal targets for anti-nematode control, as inhibitors of the enzyme could specifically target nematodes while leaving their animal and plant hosts unharmed.

Numerous analogs of fatty acids exist and some may act as specific inhibitors of enzymes such as desaturases that act on fatty acids, a fact that could be exploited for development of anti-nematode compounds. Sterculic acid, a cyclopropenoid fatty acid analog of oleic acid, is a potent inhibitor of delta-9 fatty acid desaturases (Schmid & Patterson (1998) *Lipids* 23(3):248–52; Waltermann & Steinbuchel (2000) *FEMS Microbiol Lett.* 190(1):45–50). It has also been speculated that cyclopropenoid analogs of linoleic acid may similarly inhibit delta-12 fatty acid desaturases (Dulayymi et al. (1997) *Tetrahedron* 53(3):1099–1110). It is worth noting however that malvalate, a delta-8 cyclopropene fatty acid, seems to be equally inhibitory to delta-9 desaturases in some systems, as the delta-9 cyclopropene fatty acid sterculate (Schmid & Patterson (1998) *Lipids* 23(3):248–52), demonstrating how difficult it is to predict inhibitory profiles for fatty acid analogs. Thia fatty acid analogs are also potential inhibitors of fatty acid desaturases (Skrede et al. (1997) *Biochim Biophys Acta* 1344(2):115–131; Hovik et al. (1997) *Biochim Biophys Acta* 1349(3):251–256). However, the specificity and pesticidal activity of these analogs is again difficult to predict (Beach et al. (1989) *Mol Biochem Parasitol* 35(1):57–66).

Other analogs of linoleic acid that may also be specific delta-12 inhibitors include the epoxy fatty acid (vernolic acid), the acetylenic fatty acid (crepenynic acid), or the hydroxy fatty acid (ricinoleic acid). Inhibitors that interfere with delta-12 fatty acid desaturase activity are expected to be toxic to nematodes. Importantly, fatty acid analogs such as ricinoleic, vernolic and crepenynic acid methyl esters do not appear to be toxic (or are very much less toxic) to at least some plants and are predicted not to be toxic (or are very much less toxic) to at least some animals, including mammals. Such fatty acid analogs could potentially be used in the development of nematode control agents.

Although previously expressed in plants, fatty acid analogs such as crepenynate, ricinoleate and vernolate acids were not thought to be specific inhibitors of the endogenous delta-12 desaturase desaturase (Broun & Somerville (1997) *Plant. Physiol.* 113:933–942; Singh et al. (2000) *Biochem. Society Trans.* 28(6):940–942). Changes in the ratio of oleate to linoleate in plants expressing the genes for these analogs was instead attributed to a negative interaction between the enzymes involved (Singh et al. (2001) *Planta* 212: 872–879). Addition of ricinoleate exogenously to Neurospora crassa results in a significant decrease in oleate (C18:1) and an increase in linolenate (C18:3) again providing no indication that compounds like ricinoleate were in fact specific delta-12 desaturase inhibitors (Goodrich-Tanrikulu et al. (1996) *Appl Microbiol Biotechnol.* 46(4) :382–7).

We made the surprising discovery that certain fatty acid analogs (e.g., ricinoleate, vernolate) are not only specific inhibitors of nematode delta-12 desaturases but are also nematicidal and show significantly enhanced activity over other eighteen carbon fatty acid esters such as oleate and linoleate. In contrast to short chain non-specific pesticidal fatty acid esters such as, laurate and pelargonate, these fatty acid analogs that are delta-12 desaturase inhibitors show dramatically reduced phytotoxicity and can therefore be used effectively while minimizing collateral damage to non-target organisms.

Fatty acid-based analogs or other types of inhibitors may be supplied to plants exogenously, through sprays for example. The fatty acid analogs may also be applied as a seed coat. It is also possible to provide inhibitors through a host organism or an organism on which the nematode feeds. The host organism or organism on which the nematode feeds may or may not be engineered to produce lower amounts of linoleate. For example, a host cell that does not naturally produce an inhibitor of a nematode fatty acid desaturase-like polypeptide can be transformed with genes encoding enzymes capable of making inhibitory analogs and provided with appropriate precursor chemicals exogenously if necessary. Alternatively, the active inhibitors and precursors can be made endogenously by the expression of the appropriate enzymes. In addition, yeast or other organisms can be modified to produce inhibitors. Nematodes that feed on such organisms would then be exposed to the inhibitors.

In one embodiment, transgenic cells and/or organisms could be generated that produce enzymes active on fatty acids (e.g., desaturating, hydroxylating, and/or epoxygenating enzymes). Such enzymes may be expressed, for example, in plants, vertebrates, and/or nematodes. These enzymes may produce fatty acids, analogs, or other inhibitors that can then act as specific inhibitors for other enzymes such as a fatty acid desaturase (e.g., a delta-12 epoxygenase from Crepis palaestina produces vernolic acid in transgenic *Arabidopsis*) (Singh et. al. (2000) *Biochem. Society Trans.* 28:940–942; Lee et al. (1998) *Science* 280:915–918).

The fatty acid compounds used in the invention can be applied to animals, plants or the environment of plants needing nematode control or to the food of animals needing nematode control. The compositions may be applied by, for example drench or drip techniques. With drip applications the delta-12 inhibitory fatty acid ester compounds can be applied directly to the base of the plants or the soil immediately adjacent to the plants. The composition may be applied through existing drip irrigation systems. This procedure is particularly applicable for cotton, strawberries, tomatoes, potatoes, vegetables and ornamental plants. Alternatively, a drench application can be used where a sufficient quantity of nematicidal composition is applied such that it drains to the root area of the plants. The drench technique can be used for a variety of crops and turf grasses. The drench technique can also be used for animals. Preferably, the nematicidal compositions would be administered orally to promote activity against internal parasitic nematodes. Nematicidal compositions may also be administered in some cases by injection of the host animal.

In a preferred embodiment of the subject invention, a delta-12 desaturase nematicidal inhibitory fatty acid ester will be applied as an aqueous micro-emulsion. The concentration of the nematicidal composition should be sufficient to control the nematode without causing phytotoxicity to the desired plant or undue toxicity to the animal host. An important aspect of the invention is the surprising discovery that certain fatty acid analogs (e.g., ricinoleate, vernolate) are specific inhibitors of nematode delta-12 desaturases, are nematicidal, and show significantly enhanced activity over non-specific pesticidal fatty acid esters such as oleate and linoleate, and show reduced phytotoxicity compared to non-specific short chain pesticidal fatty acid esters such as laurate and pelargonate. Thus the compositions of this invention show excellent nematicidal activity at concentrations that are not phytotoxic.

The delta-12 inhibitory nematicidal fatty acid ester compositions used according to the subject invention can be applied in conjunction with another nematicidal agent. The second agent may, for example, be applied simultaneously or sequentially. Such nematicidal agents can include for example, avermectins for animal applications.

The delta-12 inhibitory nematicidal fatty acid ester may also be coupled to an agent such as glyphosate to improve phloem mobility to the roots of plants.

The aforementioned delta-12 inhibitory nematicidal fatty acid ester compositions can be used to treat diseases or infestations caused by nematodes of the following non-limiting, exemplary genera: *Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera,* other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus,* and *Paratrichodorus, Dirofiliaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria,* and *Wuchereria.* Particularly preferred are nematodes including *Dirofilaria, Onchocerca, Brugia, Acanthocheilonema, Dipetalonema, Loa, Mansonella, Parafilaria, Setaria, Stephanofilaria,* and *Wucheria, Pratylenchus, Heterodera, Meloidogyne, Paratylenchus.* Species that are particularly preferred are: *Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita,* and *Meloidogyne arenaria, Radopholus similis, Longidorus elongatus, Meloidogyne hapla,* and *Pratylenchus penetrans.*

The following examples are, therefore, to be construed as merely illustrative, and not limitative of the remainder of the disclosure in any way whatsoever. All of the publications cited herein are hereby incorporated by reference in their entirety.

EXAMPLE 1

RNA Mediated Interference (RNAi)

A double stranded RNA (dsRNA) molecule can be used to inactivate a delta-12 fatty acid desaturase (delta-12 fat-2)

gene in a cell by a process known as RNA mediated-interference (Fire et al. (1998) *Nature* 391:806–811, and G önczy et al. (2000) *Nature* 408:331–336). The dsRNA molecule can have the nucleotide sequence of a delta-12 fat-2 nucleic acid (preferably exonic) or a fragment thereof. The dsRNA molecule can be delivered to nematodes via direct injection, or by soaking nematodes in aqueous solution containing concentrated dsRNA, or by raising bacteriovorous nematodes on *E. coli* genetically engineered to produce the dsRNA molecule.

RNAi by injection: To examine the effect of inhibiting delta-12 fat-2 activity, a dsRNA corresponding to the *C. elegans* delta-12 fat-2 gene was injected into the nematode, basically as described in Mello et al. (1991) *EMBO J.* 10:3959–3970. Briefly, a plasmid was constructed that contains a portion of the *C. elegans* delta-12 fat-2 sequence, specifically a fragment 651 nucleotides long, containing the entire first exon and terminating just before the conserved intron splice junction between the first exon and first intron. This construct encodes approximately the first 217 amino acids of the *C. elegans* delta-12 fat-2 gene. Primers were used to specifically amplify this sequence as a linear dsDNA. Single-stranded RNAs were transcribed from these fragments using T7 RNA polymerase and SP6 RNA polymerase (the RNAs correspond to the sense and antisense RNA strands). RNA was precipitated and resuspended in RNAse free water. For annealing of ssRNAs to form dsRNAs, ssRNAs were combined, heated to 95° for two minutes then allowed to cool from 70° to room temperature over 1.5–2.5 hours.

DsRNA was injected into the body cavity of 15–20 young adult *C. elegans* hermaphrodites. Worms were immobilized on an agarose pad and typically injected at a concentration of 1 mg/ml. Injections were performed with visual observation using a Zeiss Axiovert compound microscope equipped with 10× and 40× DIC objectives, for example. Needles for microinjection were prepared using a Narishige needle puller, stage micromanipulator (Leitz) and a N2-powered injector (Narishige) set at 10–20 p.s.i. After injection, 200 µl of recovery buffer (0.1% salmon sperm DNA, 4% glucose, 2.4 mM KCl, 66 mM NaCl, 3 mM CaCl2, 3 mM HEPES, pH 7.2) were added to the agarose pad and the worms were allowed to recover on the agarose pad for 0.5–4 hours. After recovery, the worms were transferred to NGM agar plates seeded with a lawn of *E. coli* strain OP50 as a food source. The following day and for 3 successive days thereafter, 7 individual healthy injected worms were transferred to new NGM plates seeded with OP50. The number of eggs laid per worm per day and the number of those eggs that hatch and reach fertile adulthood were determined. As a control, Green Fluorescent Protein (GFP) dsRNA was produced and injected using similar methods. GFP is a commonly used reporter gene originally isolated from jellyfish and is widely used in both prokaryotic and eukaryotic systems. The GFP gene is not present in the wild-type *C. elegans* genome and, therefore, GFP dsRNA does not trigger an RNAi phenotype in wild-type *C. elegans*. The *C. elegans* DELTA-12 FAT RNAi injection phenotype presented as a strongly reduced F1 hatch-rate, with the few surviving individuals arrested in an early larval stage.

RNAi by feeding: *C. elegans* can be grown on lawns of *E. coli* genetically engineered to produce double stranded RNA (dsRNA) designed to inhibit delta-12 fat-2 expression. Briefly, *E. coli* were transformed with a genomic fragment of a portion of the *C. elegans* fat-2 gene sequence, specifically a fragment 651 nucleotides long, containing the entire first exon and terminating just before the conserved intron splice junction between the first exon and first intron. This construct encodes approximately the first 217 amino acids of the *C. elegans* delta-12 FAT gene. The 651 nucleotide genomic fragment was cloned into an *E. coli* expression vector between opposing T7 polymerase promoters. The clone was then transformed into a strain of *E. coli* that carries an IPTG-inducible T7 polymerase. As a control, *E. coli* was transformed with a gene encoding the Green Fluorescent Protein (GFP). Feeding RNAi was initiated from *C. elegans* eggs or from *C. elegans* L4s. When feeding RNAi was started from *C. elegans* eggs at 23° C. on NGM plates containing IPTG and *E. coli* expressing the *C. elegans* DELTA-12 FAT or GFP dsRNA, the *C. elegans* DELTA-12 FAT RNAi feeding phenotype presented as partially sterile F1 individuals and dead F2 embryos. When feeding RNAi was started from *C. elegans* L4 larvae at 23° C. on NGM plates containing IPTG and *E. coli* expressing the *C. elegans* DELTA-12 FAT or GFP dsRNA, the *C. elegans* RNAi feeding phenotype presented as partially sterile P0 individuals (i.e., the individuals exposed initially) with developmentally arrested, sterile F1 nematodes. The sequence of the fat-2 gene is of sufficiently high complexity (i.e., unique) such that the RNAi is not likely to represent cross reactivity with other genes.

*C. elegans* cultures grown in the presence of *E. coli* expressing dsRNA and those injected with dsRNA from the delta-12 FAT gene were strongly impaired indicating that the fatty acid desaturase-like gene provides an essential function in nematodes and that dsRNA from the fatty acid desaturase-like gene is lethal when ingested by or injected into *C. elegans*.

EXAMPLE 2

Rescue of *C. elegans* DELTA-12 FAT RNAi Feeding Phenotype by Linoleic Acid Methyl Ester The *C. elegans* delta-12 fatty acid desaturase (FAT-2 protein) converts the mono-unsaturated oleic acid to the di-unsaturated fatty acid linoleic acid. The delta-12 FAT RNAi prevents expression of the delta-12 fatty acid desaturase, which is predicted to cause a decrease in levels of linoleic acid in the nematode, leading to arrested development and death. Addition of 3 mM linoleic acid methyl ester to the NGM media used for the RNAi experiment brings about a partial rescue of the DELTA-12 FAT RNAi feeding phenotype. Addition of 3 mM oleic acid methyl ester does not rescue the DELTA-12 FAT RNAi feeding phenotype (see Table 1 below).

TABLE 1

*C. elegans* delta-12 fat-2 RNAi feeding phenotypes (starting with *C. elegans* L4 larvae as the P0 animal)

| Fatty Acid Added | P0 phenotype | F1 phenotype | F2 phenotype |
|---|---|---|---|
| None | Severely reduced egg laying (almost sterile) | Developmentally arrested and sterile | NA |
| Oleic Acid Methyl Ester | Severely reduced egg laying (almost sterile) | Developmentally arrested and sterile | NA |
| Linoleic Acid Methyl Ester | Reduced egg laying | Moderately delayed development and moderately reduced egg laying | Slightly delayed development |

EXAMPLE 3

Preparation of *Caenorhabditis elegans* and Fatty Acid Methyl Esters

Mixed stage *Caenorhabditis elegans* were washed off plates seeded with OP50 bacteria using M9 solution. 250 µl of the M9 solution, which contained about 50 worms, was pipetted into each well of a 24-well plate.

Fatty acid methyl ester emulsions were prepared following the teachings of Kim et al (U.S. Pat. No. 5,698,592). Briefly, 1 ml 1% stock solution emulsions were prepared by mixing 10 μl of fatty acid methyl ester with 20 μl of the surfactant Igepal CO 630 in a 1.5 ml eppendorf tube. After careful mixing of fatty acid and Igepal CO 630, 850 μl of ddH20 was added and mixed by gentle pipetting until a homogeneous solution was obtained. Finally, 120 μl of pure isopropanol was added and mixed by gentle pipetting. This stock solution was then used to produce various fatty acid methyl ester dilution emulsions in 24-well plate assays.

EXAMPLE 4

Nematicidal Activity of Single Fatty Acid Methyl Ester Emulsions Against *Caenorhabditis elegans*

To each well, fatty acid emulsions or control emulsions were added and rapidly mixed by swirling. Nematode viability was scored by visual observation and motility assays at various time points 24 hours following addition of emulsions or controls. The fatty acid emulsions tested were methyl esters of nonanoic (pelargonic) acid, ricinoleic acid, vernolic acid, linoleic acid, oleic acid, and control emulsions lacking fatty acids.

Figure 5:
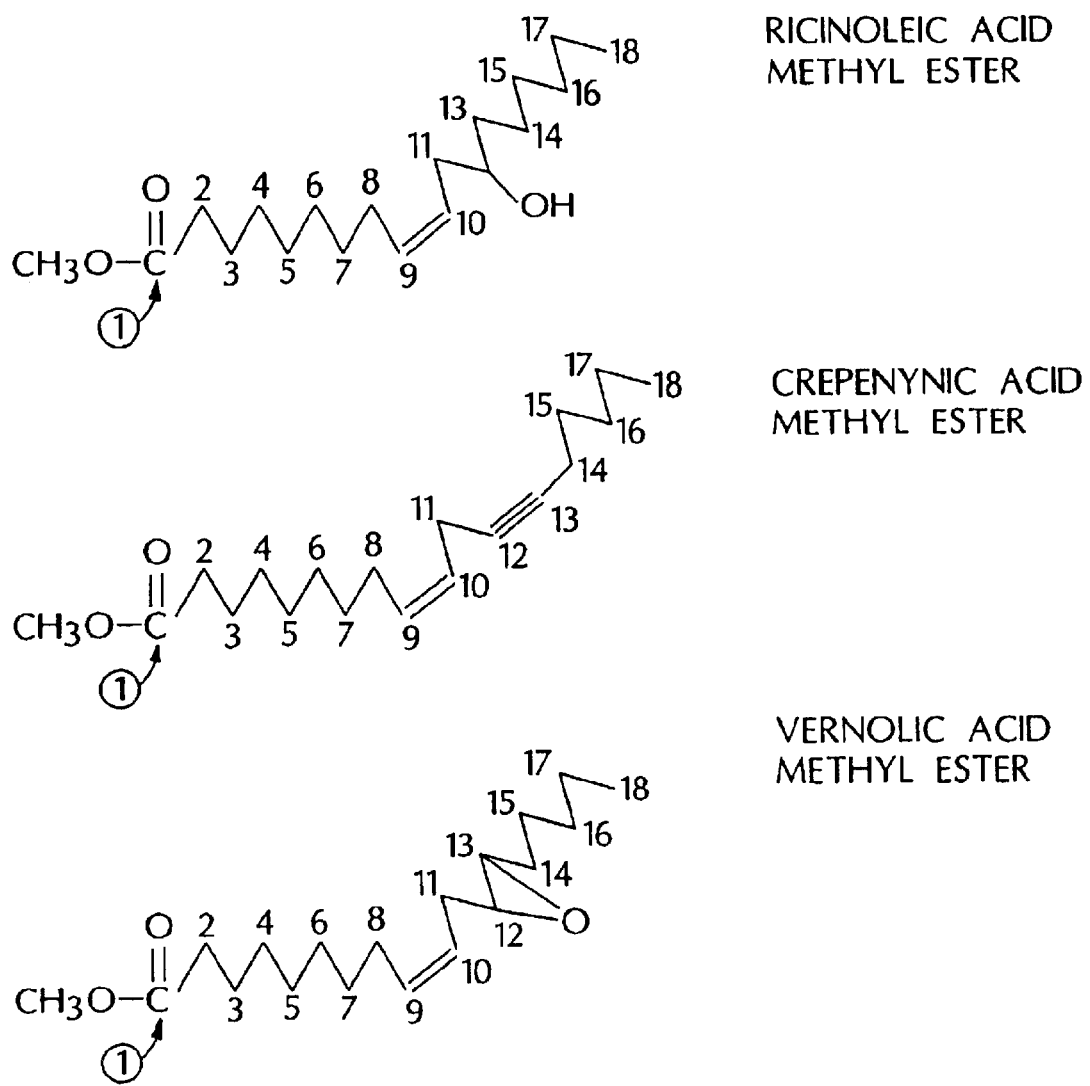
FIG. 5 is a set of drawings depicting the structures of ricinoleic acid methyl ester, crepenynic acid methyl ester, and vernolic acid methyl ester. The numbering of the carbons is indicated with the carbonyl carbon being carbon 1.

The structures of ricinoleic acid methyl ester, crepenynic acid methyl ester and vernolic acid methyl ester are depicted in FIG. 5.

| Fatty Acid | Concentration | Percentage of Worm Death | | |
|---|---|---|---|---|
| | | 1 hr | 6 hr | 24 hr |
| Nonanoic | 0.1% | 100% | 100% | 100% |
| (C9-methyl ester) | 0.003% | 50% | 50% | 50% |
| Ricinoleic Acid | 0.1% | 90% | 90% | 90% |
| (C18-methyl ester) | 0.003% | 60% | 60% | 60% |
| Vernolic Acid | 0.1% | 65% | 65% | 75% |
| (C18-methyl ester) | 0.003% | 20% | 20% | 20% |
| Linoleic Acid | 0.1% | 0–5% | 0–5% | 0–5% |
| (C18-methyl ester) | 0.003% | 0–5% | 0–5% | 0–5% |
| Oleic Acid | 0.1% | 0–5% | 0–5% | 0–5% |
| (C18-methyl ester) | 0.003% | 0–5% | 0–5% | 0–5% |
| Control | 0.1% | 0–5% | 0–5% | 0–5% |
| (no methyl ester) | 0.003% | 0–5% | 0–5% | 0–5% |

Both nonanoic and ricinoleic acid methyl ester emulsions are strongly nematicidal at a concentration of 0.1%. Nonanoic methyl ester emulsions cause an almost immediate cessation of nematode movement and subsequent death whereas ricinoleic methyl ester emulsions require up to 30 minutes before strong killing effects are apparent. However, at 0.003%, nonanoic acid methyl ester emulsions temporarily "stunned" *C. elegans*, initially giving the appearance of a 100% death phenotype. Several hours post inoculation, many nematodes recover and start moving again. This "stun" effect was not observed with the other fatty acid emulsions.

EXAMPLE 5

Preparation of Root Knot Nematode J2 Larvae (*Meloidogyne* spp.)

*Meloidogyne incognita* and *javanica* were prepared from tomato roots. The roots were bleached and the debris was separated from the J2 larvae and eggs by filtration followed by sucrose density gradient centrifugation. Eggs were hatched over 4 days at 15° C. and the J2 larvae were collected by passage though a filter, followed by centrifugation.

EXAMPLE 6

Nematicidal Activity of Fatty Acid Methyl Ester Emulsions Against Root Knot Nematodes (*Meloidogyne* spp.)

Nematodes and emulsions were incubated with shaking at room temperature for 48 hours. The contents of each well was transferred to a small spot on individual NGM plates lacking bacteria. About 24 hours after the transfer to plates, worms on and off the inoculation spot were counted as not viable or viable, respectively. Worms were considered viable if they had crawled away from the inoculation spot, or if they were moving. Worms were considered non-viable if they remained at the inoculation spot.

| Fatty acid (0.1%) | M. javanica (% not viable) | M. incognita (% not viable) |
|---|---|---|
| Vernolic Acid (C18-methyl ester) | 90% | 100% |
| Nonanoic (C9-methyl ester) | 100% | 100% |
| Ricinoleic Acid (C18-methyl ester) | 60% | 95% |
| Oleic Acid (C18-methyl ester) | 20% | 25% |

Nonanoic, vernolic and ricinoleic acid methyl ester emulsions have significant nematicidal activity against root knot nematodes (*Meloidogyne* spp.) at a concentration of 0.1%.

EXAMPLE 7

Phytotoxicity Evaluations of Fatty Acid Methyl Esters

Sterilized tomato seeds were germinated in magenta jars containing Gamborg's agar media. After two weeks of growth, seedlings were treated with 250 μl of 1% fatty acid methyl ester emulsion (nonanoic acid, ricinoleic acid, oleic acid, or a control emulsion lacking any fatty acid), applied directly to the stem-media interface. Tomato seedlings were scored at various times after application of emulsions. Of the fatty acids tested, only 1% nonanoic acid methyl ester emulsion showed obvious effects on the tomatoes. Within 18 hours of nonanoic acid emulsion application, those tomatoes showed a distinct loss of turgor pressure (wilting phenotype) and had become noticeably less green in appearance. Within 24 hours, nonanoic acid treated tomatoes were almost entirely bleached to a pale white color and had nearly totally collapsed with most leaves lying directly on the agar media surface. Importantly, none of the tomatoes treated with the other fatty acid methyl ester emulsions showed visible effects. Therefore, ricinoleic acid methyl ester shows excellent potential as an anthelmintic chemical based on its combination of high nematicidal properties combined with favorable low phytotoxicity.

What is claimed is:

1. A method for control of unwanted nematodes, the method comprising administering to mammals, plants, seed or soil a nematicidal composition comprising:

(a) an effective amount of a compound having the formula

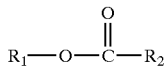

wherein:
R$_1$=a C1–C5 substituted or unsubstituted carbon chain, wherein the substituents are selected from the group consisting of:
 i) hydroxy,
 ii) halogen,
 iii) amino,
 vi) cyano,
 v) cyclopropane,
 vi) cyclopropene,
 vii) epoxy, and
 viii) a substituted or unsubstituted C1–C2 carbon chain, wherein the substituents on the C1–C2 carbon chain selected from the group consisting of hydroxy, halogen, amino, cyano, and epoxy;
R$_2$=a C15–C19 substituted or unsubstituted carbon chain having a cis double bond between the 9$^{th}$ and 10$^{th}$ carbons counting from the carbonyl carbon and either, (i) a triple bond between the 12$^{th}$ and 13$^{th}$ carbons counting from the carbonyl carbon or (ii) either a single or double bond between the 12$^{th}$ and 13$^{th}$ carbons counting from the carbonyl carbon and at least one substituant at one or both of the 12$^{th}$ and 13$^{th}$ carbons counting from the carbonyl carbon, wherein the substituants are selected from the group consisting of:
 i) hydroxy,
 ii) halogen,
 iii) amino,
 vi) cyano,
 v) cyclopropane,
 vi) cyclopropene,
 vii) epoxy, and
 viii) a substituted or unsubstituted C1–C2 carbon chain, wherein the substituents on the C1–C2 carbon chain are selected from the group consisting of hydroxy, halogen, amino, cyano, and epoxy; and
(b) an aqueous surfactant;
whereby unwanted nematodes are controlled.

2. The method of claim 1 wherein R$_1$=a C1–C5 substituted or unsubstituted carbon chain, wherein the substituants are selected from the group consisting of:
 i) hydroxy,
 ii) halogen,
 iii) amino,
 vi) cyano,
 v) cyclopropane,
 vi) cyclopropene,
 vii) epoxy, and
 viii) an unsubstituted C1–C2 carbon chain.

3. The method of claim 1 wherein R$_2$=a C15–C19 substituted or unsubstituted carbon chain having a cis double bond between the 9$^{th}$ and 10$^{th}$ carbons counting from the carbonyl carbon and either: (i) a triple bond between the 12$^{th}$ and 13$^{th}$ carbons counting from the carbonyl carbon or (ii) either a single or double bond between the 12$^{th}$ and 13$^{th}$ carbons and at least one substituant at one or both of the 12$^{th}$ and 13$^{th}$ carbons counting from the carbonyl carbon, wherein the substituants are selected from the group consisting of:
 i) hydroxy,
 ii) halogen,
 iii) amino,
 vi) cyano,
 v) cyclopropane,
 vi) cyclopropene,
 vii) epoxy, and
 viii) an unsubstituted C1–C2 carbon chain.

4. The method of claim 1 wherein R$_1$ is a C1–C2 substituted or unsubstituted carbon chain.

5. The method of claim 1 wherein R$_2$ is substituted only at one or both of 12$^{th}$ and 13$^{th}$ carbons.

6. The method of claim 1 wherein R$_2$ is substituted only at the 12$^{th}$ carbon.

7. The method of claim 1 wherein within R$_2$ the substituants are selected from the group consisting of:
 i) hydroxy,
 ii) epoxy, and
 iii) a C1 alkyl.

8. The method of claim 1 wherein the nematode infects plants and the nematicidal composition is applied to the soil or to plants.

9. The method of claim 8 wherein the nematicidal composition is applied to soil before planting.

10. The method according to claim 8 where the nematicidal composition is applied to soil after planting.

11. The method of claim 8 wherein the nematicidal composition is applied to soil using a drip system.

12. The method of claim 8 wherein the nematicidal composition is applied to soil using a drench system.

13. The method of claim 8 wherein the nematicidal composition is applied to plant roots.

14. The method of claim 1 wherein the nematicidal composition is applied to seeds.

15. The method of claim 1 wherein the nematode infects a mammal.

16. The method of claim 1 wherein the nematicidal composition is administered to non-human mammal.

17. The method of claim 1 wherein the nematicidal composition is administered to a human.

18. The method of claim 16 wherein the nematicidal composition is formulated as a drench to be administered to a non-human animal.

19. The method of claim 15 wherein the nematicidal composition is formulated as an orally administered drug.

20. The method of claim 15 wherein the nematicidal composition is formulated as an injectable drug.

21. A method for control of unwanted nematodes, the method comprising administering to mammals, plants, seeds or soil a nematicidal composition comprising an effective amount of:
 (a) a fatty acid methyl ester selected from the group consisting of: ricinoleic acid methyl ester, crepenynic acid methyl ester, and vernolic acid methyl ester, and
 (b) an aqueous surfactant;
whereby unwanted nematodes are controlled.

22. The method of claim 1 or claim 21 wherein the aqueous surfactant is selected from the group consisting of: ethyl lactate, polyoxyethylene sorbitan 20 monolaureate, polyoxyethylene 9 nonylphenyl ether.

23. The method of claim 1 or claim 21 wherein the composition further comprises:
 (c) a permeation enhancer.

24. The method of claim 23 wherein the permeation enhancer is a cyclodextrin.

25. The method of claim 1 or 21 wherein the composition further comprises:
(c) a co-solvent.
26. The method of claim 25 wherein the co-solvent is isopropanol.
27. The method of claim 1 or claim 21 further comprising administering a nematicide selected from the group consisting of: avermectins, ivermectin, and milbemycin.
28. A nematicidal composition comprising:
(a) an effective amount of a compound having the formula

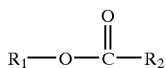

wherein:
$R_1$=a C1–C5 substituted or unsubstituted carbon chain, wherein the substituents are selected from the group consisting of:
i) hydroxy,
ii) halogen,
iii) amino,
vi) cyano,
v) cyclopropane,
vi) cyclopropene,
vii) epoxy, and
viii) a substituted or unsubstituted C1–C2 carbon chain, wherein the substituents on the C1–C2 carbon chain are selected from the group consisting of hydroxy, halogen, amino, cyano, and epoxy; and
$R_2$=a C15–C19 substituted or unsubstituted carbon chain having a cis double bond between the $9^{th}$ and $10^{th}$ carbons counting from the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituents are selected from the group consisting of:
i) hydroxy,
ii) halogen,
iii) amino,
vi) cyano,
v) cyclopropane,
vi) cyclopropene,
vii) epoxy, and
viii) a substituted or unsubstituted C1–C2 carbon chain, wherein the substituents on the C1–C2 carbon chain are selected from the group consisting of hydroxy, halogen, amino, cyano, and epoxy;
(b) an aqueous surfactant; and
(c) a nematicide selected from the group consisting of: avermectins, ivermectin, and milbemycin.
29. The composition of claim 28 wherein the aqueous surfactant is selected from the group consisting of: ethyl lactate, polyoxyethylene 20 sorbitan monolaureate, polyoxyethylene 9 nonylphenyl ether.
30. The composition of claim 28 further comprising a permeation enhancer.
31. The composition of claim 28 further comprising a co-solvent.
32. The nematicidal composition of claim 31 wherein the co-solvent is isopropanol.
33. The nematicidal composition of claim 28 wherein $R_1$=a C1–C5 substituted or unsubstituted carbon chain, wherein the substituents are selected from the group consisting of:
i) hydroxy,
ii) halogen,
iii) amino,
vi) cyano,
v) cyclopropane,
vi) cyclopropene,
vii) epoxy, and
viii) an C1–C2 carbon chain.
34. The nematicidal composition of claim 28 wherein $R_2$=a C15–C19 substituted or unsubstituted carbon chain having a cis double bond between the $9^{th}$ and $10^{th}$ carbons counting from he carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituents are selected from the group consisting of:
i) hydroxy,
ii) halogen,
iii) amino,
vi) cyano,
v) cyclopropane,
vi) cyclopropene,
vii) epoxy, and
viii) an unsubstituted C1–C2 carbon chain.
35. The nematicidal composition of claim 28 wherein $R_1$ is a C1–C2 substituted or unsubstituted carbon chain.
36. The nematicidal composition of claim 28 wherein $R_2$ is substituted only at one or both of $12^{th}$ and $13^{th}$ carbons counting from the carbonyl carbon.
37. The nematicidal composition of claim 36 wherein $R_2$ is substituted only at the $12^{th}$ carbon counting from the carbonyl carbon.
38. The composition of claim 36 wherein within $R_2$ the substituents are selected from the group consisting of:
i) hydroxy,
ii) epoxy, and
iii) a C1 alkyl.
39. The nematicidal composition of any of claims 33–38 wherein the aqueous surfactant is selected from the group consisting of: ethyl lactate, polyoxyethylene 20 sorbitan monolaureate, polyoxyethylene 9 nonylphenyl ether.
40. The nematicidal composition of any of claims 33–38 further comprising a co-solvent.
41. A nematicidal composition consisting essentially of:
(a) an effective amount of a compound having the formula

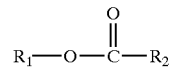

wherein:
$R_1$=a C1–C5 substituted or unsubstituted carbon chain, wherein the substituents are selected from the group consisting of:
i) hydroxy,
ii) halogen,
iii) amino,
vi) cyano,
v) cyclopropane,
vi) cyclopropene, vii) epoxy, and viii) a substituted or unsubstituted C1–C2 carbon chain, wherein the substituents on the C1–C2 carbon chain are selected from the group consisting of hydroxy, halogen, amino, cyano, and epoxy; and $R_2$=a C15–C19 substituted or unsubstituted carbon chain having a cis double bond between the $9^{th}$ and $10^{th}$ carbons counting from the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, i) hydroxy,
ii) halogen,
iii) amino,
vi) cyano,
v) cyclopropane,
vi) cyclopropene,
vii) epoxy, and
viii) a substituted or unsubstituted C1–C2 carbon chain, wherein the substituents on the C1–C2 carbon chain are selected from the group consisting of hydroxy, halogen, amino, cyano, and epoxy; and (b) an aqueous surfactant selected from the group consisting of: ethyl lactate, polyoxyethylene 20 sorbitan monolaureate, polyoxyethylene 9 nonylphenyl ether.

42. Tho nematicidal composition of claim 41 wherein $R_1$=a C1–C5 substituted or unsubstituted carbon chain, wherein the substituents are selected from the group consisting of:

i) hydroxy,
ii) halogen,
iii) amino,
vi) cyano,
v) cyclopropane,
vi) cyclopropene,
vii) epoxy, and
viii) an unsubstituted C1–C2 carbon chain.

43. The nematicidal composition of claim 41 wherein $R_2$=a C15–C19 substituted or unsubstituted carbon chain having a cis double bond between the $9^{th}$ and $10^{th}$ carbons counting from the carbonyl carbon and either: (i) a triple bond between the $12^{th}$ and $13^{th}$ carbons counting from the carbonyl carbon or (ii) either a single or double bond between $12^{th}$ and $13^{th}$ carbons counting from the carbonyl carbon and at least one substituant at one or both of the $12^{th}$ and $13^{th}$ carbons counting from the carbonyl carbon, wherein the substituants are selected from the group consisting of:

i) hydroxy,
ii) halogen,
iii) amino,
vi) cyano,
v) cyclopropane,
vi) cyclopropene,
vii) epoxy, and
viii) an unsubstituted C1–C2 carbon chain.

44. The composition of claim 41 wherein $R_1$ is C1–C2 substituted or unsubstituted carbon chain.

45. The composition of claim 41 wherein $R_2$ is substituted only at one or both of $12^{th}$ and $13^{th}$ carbons counting from the carbonyl carbon.

46. The composition of claim 41 wherein $R_1$ is substituted only at the $12^{th}$ carbon counting from the carbonyl carbon.

47. The composition of claim 46 wherein within $R_2$ the substituants are selected from the group consisting of:

i) hydroxy,
vii) epoxy, and
iii) a C1 alkyl.

48. A nematicidal feed for a non-human mammal comprising:

(a) a feed selected from the group consisting of: soy, wheat corn, sorghum, millet, alfalfa, clover, and rye;

(b) an effective amount of a nematicidal compound having the formula

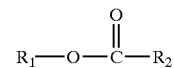

wherein:

$R_1$=a C1–C5 substituted or unsubstituted carbon chain, wherein the substituants are selected from the group consisting of:
i) hydroxy,
ii) halogen,
iii) amino,
vi) cyano,
v) cyclopropane,
vi) cyclopropene,
vii) epoxy, and
viii) a substituted or unsubstituted C1–C2 carbon chain, wherein the substituents on the C1–C2 carbon chain are selected from the group consisting of hydroxy, halogen, amino, cyano, and epoxy;

and $R_2$=a C1–$C_{19}$ substituted or unsubstituted carbon chain having a cis double bond between the $9^{th}$ and $10^{th}$ carbons and either: (i) a triple bond between the $12^{th}$ and $13^{th}$ carbons or (ii) either a single or double bond between the $12^{th}$ and $13^{th}$ carbons and at least one substituant at one or both of the $12^{th}$ and $13^{th}$ carbons, wherein the substituants are selected from the group consisting of:

i) hydroxy,
ii) halogen,
iii) amino,
vi) cyano,
v) cyclopropane,
vi) cyclopropene,
vii) epoxy, and
viii) a substituted or unsubstituted C1–C2 carbon chain, wherein the substituents on the C1–C2 carbon chain are selected from the group consisting of hydroxy, halogen, amino, cyano, and epoxy; and (c) an aqueous surfactant.

49. The nematicidal feed of claim 48 wherein $R_1$=a C1–C5 substituted or unsubstituted carbon chain, wherein the substituants are selected from the group consisting of:

i) hydroxy,
ii) halogen,
iii) amino,
vi) cyano,
v) cyclopropane,
vi) cyclopropene,
vii) epoxy, and
viii) an unsubstituted C1–C2 carbon chain.

50. The nematicidal feed of claim 48 wherein $R_2$=a C15–C19 substituted or unsubstituted carbon chain having a cis double bond between the $9^{th}$ and $10^{th}$ carbons counting from the carbonyl carbon and either: (i) a triple bond between the $12^{th}$ and $13^{th}$ carbons counting from the carbonyl carbon or (ii) either a single or double bond between the $12^{th}$ and $13^{th}$ carbons counting from the carbonyl carbon and at least one substituant at one or both of the $12^{th}$ and $13^{th}$ carbons counting from the carbonyl carbon, wherein the substituants are selected from the group consisting of:

i) hydroxy,
ii) halogen,
iii) amino,
vi) cyano,
v) cyclopropane,
vi) cyclopropene,
vii) epoxy, and
viii) an unsubstituted C1–C2 carbon chain.

51. The nematicidal feed of claim 48 wherein $R_1$ is a C1–C2 substituted or unsubstituted carbon chain.

52. The nematicidal feed of claim 48 wherein $R_2$ is substituted only at one or both of $12^{th}$ and $13^{th}$ carbons counting from the carbonyl carbon.

53. The nematicidal feed of claim 52 wherein $R_2$ is substituted only at the $12^{th}$ carbon counting from the carbonyl carbon.

54. The nematicidal feed of claim 52 wherein within $R_2$ the substituants are selected from the group consisting of:

i) hydroxy,
ii) epoxy, and
iii) a C1 alkyl.

55. A nematicidal feed for a non-human mammal comprising:

(a) a feed selected from the group consisting of: soy, wheat, corn, sorghum, millet, alfalfa, clover, and rye;
(b) a fatty acid methyl ester selected from the group consisting of: ricinoleic acid methyl ester, crepenynic acid methyl ester, and vernolic acid methyl ester; and
(c) an aqueous surfactant.

* * * * *

UNITED STATES PATENT AND TRADEMARK OFFICE
CERTIFICATE OF CORRECTION

PATENT NO. : 6,887,900 B2
APPLICATION NO. : 10/090527
DATED : May 3, 2005
INVENTOR(S) : Deryck J. Williams, Andrew P. Kloek and Michelle Coutu Hresko It is certified that error appears in the above-identified patent and that said Letters Patent is hereby corrected as shown below:

Column 22, Claim 1, Line 66:
Delete "seed" and Insert --seeds--

Column 23, Claim 1, Line 14:
Delete "vi" and Insert --iv--

Column 23, Claim 1, Line 19:
Insert --are-- after "chain"

Column 23, Claim 1, Line 35:
Delete "vi" and Insert --iv--

Column 23, Claim 2, Line 53:
Delete "vi" and Insert --iv--

Column 24, Claim 3, Line 4:
Delete "vi" and Insert --iv--

Column 25, Claim 28, Line 23:
Delete "vi" and Insert --iv--

Column 25, Claim 28, Line 43:
Delete "vi" and Insert --iv--

Column 26, Claim 33, Line 5:
Delete "vi" and Insert --iv--

Column 26, Claim 34, Line 25:
Delete "vi" and Insert --iv--

Column 26, Claim 41, Line 65:
Delete "vi" and Insert --iv--

UNITED STATES PATENT AND TRADEMARK OFFICE
CERTIFICATE OF CORRECTION

| | | |
|---|---|---|
| PATENT NO. | : 6,887,900 B2 | |
| APPLICATION NO. | : 10/090527 | |
| DATED | : May 3, 2005 | |
| INVENTOR(S) | : Deryck J. Williams, Andrew P. Kloek and Michelle Coutu Hresko | |

It is certified that error appears in the above-identified patent and that said Letters Patent is hereby corrected as shown below:

Column 27, Claim 41, Line 14:
After "carbon," Insert --wherein the substituants are selected from the group consisting of:--

Column 27, Claim 41, Line 18:
Delete "vi" and Insert --iv--

Column 27, Claim 42, Line 29:
Delete "tho" and Insert --the--

Column 27, Claim 42, Line 37:
Delete "vi" and Insert --iv--

Column 27, Claim 43, Line 57:
Delete "vi" and Insert --iv--

Column 28, Claim 46, Line 1:
Delete "$R_1$" and Insert --$R_2$--

Column 28, Claim 48, Line 11:
Delete "wheat" and Insert --wheat,--

Column 28, Claim 48, Line 27:
Delete "vi" and Insert --iv--

Column 28, Claim 48, Line 36:
Delete "Cl-$C_{19}$" and Insert --C15-C19--

Column 28, Claim 48, Line 47:
Delete "vi" and Insert --iv--

UNITED STATES PATENT AND TRADEMARK OFFICE
CERTIFICATE OF CORRECTION

PATENT NO. : 6,887,900 B2
APPLICATION NO. : 10/090527
DATED : May 3, 2005
INVENTOR(S) : Deryck J. Williams, Andrew P. Kloek and Michelle Coutu Hresko It is certified that error appears in the above-identified patent and that said Letters Patent is hereby corrected as shown below:

Column 28, Claim 49, Line 63:
Delete "vi" and Insert --iv--

Column 29, Claim 50, Line 15:
Delete "vi" and Insert --iv--

Signed and Sealed this

Fourteenth Day of April, 2009

JOHN DOLL
*Acting Director of the United States Patent and Trademark Office*